United States Patent [19]
Blank et al.

[11] 3,963,733
[45] June 15, 1976

[54] 3-(P-METHOXYBENZYLTHIO)2-NON-OXOCARBONYLIC PYRIDINES

[75] Inventors: Benjamin Blank, Trevose; John G. Gleason, Cornwell Heights, both of Pa.

[73] Assignee: SmithKline Corporation, Philadelphia, Pa.

[22] Filed: Dec. 5, 1974

[21] Appl. No.: 529,785

Related U.S. Application Data

[62] Division of Ser. No. 363,237, May 23, 1973, Pat. No. 3,873,552.

[52] U.S. Cl. ........................................ 260/294.8 G
[51] Int. Cl.² ............. C07D 213/79; C07D 213/81
[58] Field of Search .............................. 260/294.8 G

[56] References Cited
UNITED STATES PATENTS 3,639,413 2/1972 Domenico ..................... 260/294.8
3,860,716 1/1975 Berkoff et al ..................... 424/266

*Primary Examiner*—Natalie Trousof
*Assistant Examiner*—R. W. Ramsuer
*Attorney, Agent, or Firm*—Joan S. Keps; Richard D. Foggio; William H. Edgerton

[57] ABSTRACT

3-Thiolpicolinic acid is prepared by reacting a 3-halopyridine, having a 2-substituent which is hydrolyzable to a carboxy group, with an alkali metal salt of p-methoxybenzyl mercaptan, hydrolyzing the 2-substituent to a carboxy group and then cleaving the p-methoxybenzyl group under non-reductive acid conditions. The 3-(p-methoxybenzylthio)pyridines substituted in the 2-position by a carboxy group or a group which is hydrolyzable to a carboxy group are new intermediates.

1 Claim, No Drawings

3-(P-METHOXYBENZYLTHIO)2-NON-OXOCARBONYLIC PYRIDINES

This is a division of app. Ser. No. 363,237 filed May 23, 1973, now U.S. Pat. No. 3,873,532.

This invention relates to a new process of preparing 3-thiolpicolinic acid and new intermediates in the process.

The process of this invention is represented schematically as follows.

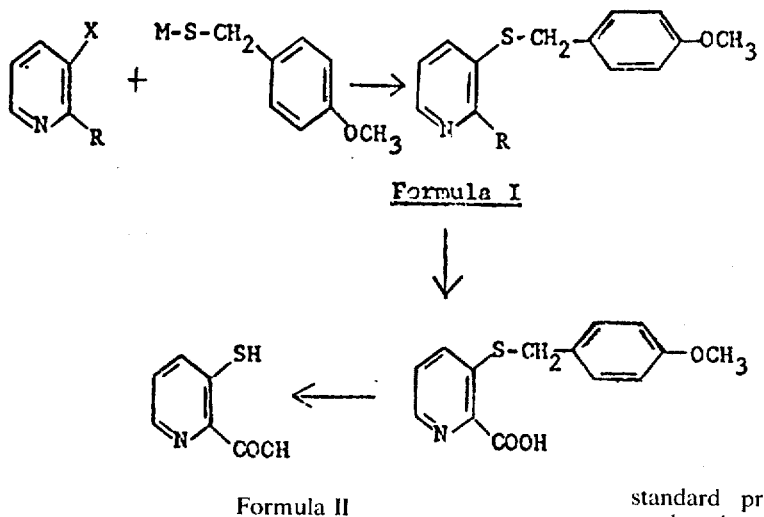

Formula II in which:

R is a group which is hydrolyzable to a carboxy group, for example COO-lower alkyl, CN, CONH$_2$ or

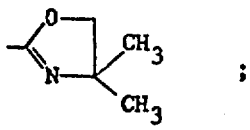

X is halo and
M is an alkali metal.

The intermediates of Formulas I and II which are represented by the following formula are also objects of this invention.

Formula III

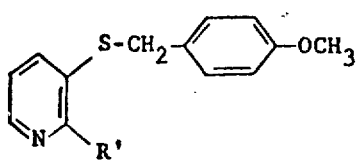

in which R' is carboxy or a group which is hydrolyzable to a carboxy group, for example COO-lower alkyl, CN,

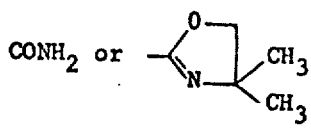

According to the above process a 3-halopyridine having a substituent in the 2-position which is hydrolyzable to a carboxy group is reacted with an alkali metal salt of p-methoxybenzyl mercaptan to give the 2-substituted-3-(p-methoxybenzylthio)pyridine intermediates of Formula I. This reaction is preferably carried out in an aprotic, polar solvent such as dimethylsulfoxide, dimethylformamide, tetrahydrofuran, dimethoxyethane or diglyme at elevated temperature, for example at about 60°–100°C. The 2-substituent of the intermediate of Formula I is hydrolyzed to a carboxy group by standard procedures for hydrolysis to give 3-(p-methoxybenzylthio)picolinic acid which is the compound of Formula II. The p-methoxybenzyl group is cleaved under non-reductive acid conditions for example with mercuric acetate in formic acid or in trifluoroacetic acid.

The 2-substituent which is hydrolyzable to a carboxy group is, for example, an ester, nitrile, amide or dimethyloxazoline group. The hydrolysis of the 2-substituent is accomplished by standard procedures, for example the esters are hydrolyzed by treating with aqueous base such as aqueous sodium hydroxide preferably at elevated temperatures, for example for about two hours, the nitriles and amides are hydrolyzed by heating with base, for example for about 6–40 hours and the dimethyloxazoline is hydrolyzed by treating with acid, for example hydrochloric acid and then heating the resulting aminoalkyl ester with aqueous base, for example aqueous sodium hydroxide.

Alternatively, but less preferably, the hydrolysis of the ester, nitrile, amide or dimethyloxazoline groups to the carboxy group may be carried out after cleaving off the p-methoxybenzyl group.

The compound prepared by the process of this invention, that is 3-thiolpicolinic acid, has pharmacological activity. This compound inhibits gluconeogenesis and therefore reduces the level of blood sugar in animals and results in useful hypoglycemia for the treatment of diabetes. The ability of 3-thiolpicolinic acid to inhibit gluconeogenesis from lactate is measured in vitro using slices of both renal cortex and liver from fasted rats. This compound reduces renal gluconeogenesis by 52% at a concentration of $1 \times 10^{-5}$ Molar and using liver slices produces an 82% inhibition at $1 \times 10^{-4}$ Molar. In the isolated perfused rat liver, at a concentration of $1 \times 10^{-4}$ Molar, inhibition is 40% when lactate is added as exogenous substrate.

The hypoglycemic activity is measured in the 48-hour-fasted, normal rat after a single dose of from 25 mg./kg. to 300 mg./kg. of 3-thiolpicolinic acid, administered orally or intraperitoneally. With 3-thiolpicolinic acid at oral doses of 25, 50, 100 or 150 mg./kg. there is a significant reduction in blood glucose, compared to the control animals, at one hour post-treatment. At two hours animals dosed with 25 mg./kg. or 50 mg./kg. recover and by the fifth hour animals treated with 100 mg./kg. recover. Five hours post-treatment, animals dosed with 150 mg./kg. continue to have a significantly reduced level of blood sugar.

The following examples are not limiting but are illustrative of the process and intermediates of this invention.

EXAMPLE 1

3-Bromopicolinic acid (5 g.) is stirred and refluxed under nitrogen with 40 ml. of 14% boron trifluoride in methanol. the solution is cooled and the methanol is evaporated. The residue is dissolved in chloroform. The chloroform extracts are washed with 5% aqueous sodium bicarbonate solution and water, then the organic solution is dried and evaporated. The residue is recrystallized from cyclohexane to give methyl 3-bromopicolinate, m.p. 34°–36°C.

A solution of 30 g. (0.19 m.) of p-methoxybenzyl mercaptan in 25 ml. of dimethylsulfoxide is added to a stirred suspension of 8 g. (0.14 m.) of 55% sodium hydride in in 100 ml. of dry dimethylsulfoxide under nitrogen at such a rate that the temperature is kept below 20°C. The mixture is stirred for one hour at room temperature and then 34 g. (0.16 m.) of methyl 3-bromopicolinate is added. The mixture is kept at 70°–90°C. for 2–3 hours, then cooled and diluted with ice water. The resulting solid is filtered, washed with water, dried, and recrystallized from carbon tetrachloride to give methyl 3-(p-methoxybenzlthio)-picolinate, m.p. 98–100°C.

To a solution of 3 g. of methyl 3-(p-methoxybenzylthio)picolinate in 50 ml. of ethanol is added 10 ml. of 20% aqueous sodium hydroxide solution and the mixture is warmed on a steam bath for two hours. The alcohol is evaporated off and the residue is cooled and acidified with dilute hydrochloric acid. The precipitate is filtered off, washed with water, dried and recrystallized from methanol to give 3-(p-methoxybenzylthio)-picolinic acid, m.p. 170°–172°C.

To a solution of 3.3 g. (0.012 m.) of 3-(p-methoxybenzylthio)picolinic acid in 60 ml. of 90% formic acid under nitrogen is added a solution of 10.8 g. of mercuric acetate in 50 ml. of water. The mixture is stirred for 30 minutes at room temperature. The resulting precipitate is filtered off, washed with water and resuspended in water. The suspension is saturated with hydrogen sulfide and the precipitated mercuric sulfide is filtered off. The filtrate is evaporated and the residue is recrystallized from water to give 3-thiolpicolinic acid.

EXAMPLE 2

A solution of 4 g. (0.02 mole) of 3-bromopicolinic acid in 200 ml. of chloroform (dried over calcium chloride) is stirred under reflux and 20 ml. of thionyl chloride is added dropwise. The resulting mixture is heated for 4.5 hours, then concentrated. The residue is evaporated with toluene, then dissolved in acetone. The acetone solution is added to cold aqueous ammonia. The precipitate is filtered, washed with water, and recrystallized to give 3-bromopicolinamide.

By the procedure of Efxample 1, a solution of p-methoxybenzyl mercaptan in dimethylsulfoxide is added slowly to a stirred suspension of sodium hydride in dry dimethylsulfoxide under nitrogen. After stirring for one hour at room temperature, 3-bromopicolinamide is added and the mixture is kept about 75°C. for three hours, then worked up by cooling, diluting with ice water, filtering off the resulting solid, washing it with water, drying and recrystallizing from aqueous dimethylformamide to give 3-(p-methoxybenzylthio)-picolinamide, m.p. 252°C. (dec.).

A suspension of 5 g. of 3-(p-methoxybenzylthio)-picolinamide in 50 ml. of 20% aqueous sodium hydroxide is refluxed for about 24 hours, then cooled and acidified with dilute hydrochloric acid. Filtering, washing the precipitate with water, drying and recrystallizing from methanol gives 3-(p-methoxybenzylthio)picolinic acid.

To a solution of 8 g. (.003 m.) of 3-(p-methoxybenzylthio)picolinic acid in 15 ml. of trifluoroacetic acid under nitrogen is added a solutiqn of 4 g. of mercuric acetate in 30 ml. of trifluoroacetic acid. The resulting mixture is stirred at room temperature for three hours under nitrogen. The solution is saturated with hydrogen sulfide and the precipitated mercuric sulfide is filtered and washed with trifluoroacetic acid. The combined filtrate and washings are taken to dryness. The residue is partitioned between water and benzene. The benzene phase is extracted twice with dilute hydrochloric acid and the combined aqueous phases are evaporated. The residual hydrochloride salt is recrystallized from boiling water whereupon it is converted to the free 3-thiolpicolinic acid.

EXAMPLE 3

3-Bromopicolinamide, prepared as in Example 2, (4 g.) is heated with 100 ml. of acetic anhydride on a steam bath. The mixture is then concentrated and worked up by diluting and triturating with water. The solid is dried and sublimed to give 3-bromopicolinonitrile.

A solution of 4.6 g. of p-methoxybenzyl mercaptan in 10 ml. of dimethylsulfoxide is added slowly with cooling to a stirred suspension of sodium hydride in dry dimethylsulfoxide under nitrogen. After the mixture is stirred for one hour at room temperature, 4.6 g. of 3-bromopicolinonitrile is added and the mixture is kept at about 75°C. for three hours to give, after working up as in Example 2, 3-(p-methoxybenzylthio)picolinonitrile, m.p. 97°–99°C.

The above prepared nitrile is dissolved n ethanol and the solution is treated with an excess of 20% aqueous sodium hydroxide solution. The mixture is warmed on a steam bath for about 20 hours, the alcohol is evaporated and the residue is cooled and acidified with dilute hydrochloric acid. Filtering, washing the precipitate with water, drying and recrystallizing from methanol gives 3-(p-methoxybenzylthio)picolinic acid.

The p-methoxybenzylthio group of the above prepared 3-(p-methoxybenzylthio)picolinic acid is cleaved with mercuric acetate in trifluoroacetic acid by the procedure of Example 2 to give 3-thiolpicolinic acid.

EXAMPLE 4

3-Chloropicolinic acid is esterified using boron trifluoride and ethanol by the procedure described in Example 1 to give ethyl 3-chloropicolinate.

By the procedure of Example 1, the above prepared ethyl 3-chloropicolinate is converted to ethyl 3-(p-methoxybenzylthio)picolinate.

The ethyl 3-(p-methoxybenzylthio)picolinate is hydrolyzed by treating with 20% aqueous sodium hydroxide solution and warming on a steam bath for two hours. the p-methoxybenzylthio group of the resulting 3-(p-methoxybenzylthio)picolinic acid is cleaved with mercuric acetate in 90% formic acid by the procedure of Example 1 to give 3-thiolpicolinic acid.

EXAMPLE 5

A solution of 5.0 g. of 3-bromopicolinoyl chloride (prepared by refluxing 3-bromopicolinic acid with thionyl chloride by the procedure of Example 2) in 25 ml. of dichloromethane is added to a solution of 3.9 g. of 2-amino-2-methylpropanol in 25 ml. of dichloromethane at 0°C. The resulting hydroxyalkylpicolinamide is cyclized by refluxing with thionyl chloride by the method of Leffler and Adams, J. Am. Chem. Soc. 59:2252 (1937) and the resulting hydrochloride salt is neutralized with aqueous sodium hydroxide solution to give 3-bromo-2-(4,4-dimethyl-2-oxazolinyl)pyridine.

The above prepared 3-bromo-2-(4,4-dimethyl-2-oxazolinyl)pyridine is reacted with the sodium salt of p-methoxybenzyl mercaptan by the procedure of Example 1 to give 2-(4,4-dimethyl-2-oxazolinyl)-3-(p-methoxybenzylthio)pyridine.

Two grams of 2-(4,4-dimethyl-2-oxazolinyl)-3-(p-methoxybenzylthio)pyridine is heated with 50 ml. of 3N hydrochloric acid for 10 minutes. The mixture is filtered and the solid material is heated with 50 ml. of aqueous methanol (50%) containing 20% sodium hydroxide for 30 minutes. The mixture is concentrated, acidified with dilute hydrochloric acid and filtered to give 3-(p-methoxybenzylthio)picolinic acid. The p-methoxybenzylthio group is cleaved with mercuric acetate in 90% formic acid by the procedure of Example 1 to give 3-thiolpicolinic acid.

What is claimed is:

1. A compound of the formula:

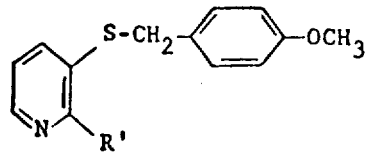

in which R' is carboxy, COO-lower alkyl or CONH$_2$.

* * * * *